United States Patent [19]

Houlihan

[11] 4,036,978

[45] July 19, 1977

[54] ETHANODIBENZOINDOLES

[75] Inventor: William J. Houlihan, Mountain Lakes, N.J.

[73] Assignee: Sandoz, Inc., E. Hanover, N.J.

[21] Appl. No.: 683,920

[22] Filed: May 6, 1976

[51] Int. Cl.$^2$ .................... C07D 209/58; A61K 31/40
[52] U.S. Cl. ................................ 424/274; 260/313.1; 260/326.5 B; 260/558 D
[58] Field of Search ...................... 260/313.1; 424/274

[56] References Cited

U.S. PATENT DOCUMENTS 3,725,436  4/1973  Butler .............................. 260/326.11

*Primary Examiner*—Raymond V. Rush
*Attorney, Agent, or Firm*—Gerald D. Sharkin; Robert S. Honor; Thomas O. McGovern

[57] ABSTRACT

Substituted and unsubstituted ethanodibenzoindoles, for example, 3-chloro-1-methyl-1,2-dihydro-6,10b-ethanodibenzo[cd,g] indole, are prepared by cyclizing and reducing N-naphthylbenzamides and are useful as anti-inflammatory agents.

4 Claims, No Drawings

ETHANODIBENZOINDOLES

This invention relates to 6,10b-ethanodibenzo[cd,g] indoles, processes and intermediates for their preparation and their use in pharmaceutical compositions.

The compounds of this invention may be represented by the following structural formula (I):

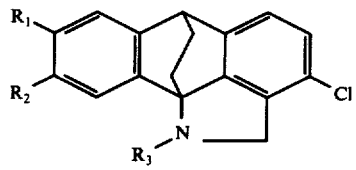

where
R₁ and R₂ each independently are hydrogen or straight chain lower alkyl of 1 to 3 carbon atoms and
R₃ is methyl or ethyl
and pharmaceutically acceptable acid addition salts thereof.

The compound of formula I may be prepared in accordance with the following reaction scheme:

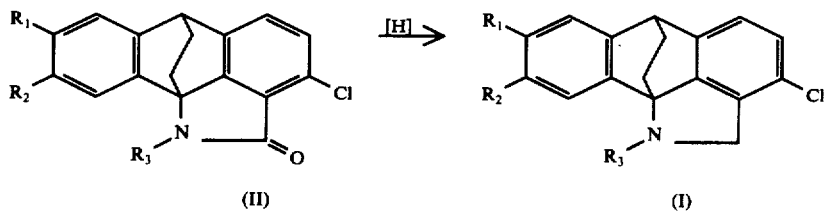

where R₁, R₂, and R₃ are as defined above.

The compounds of formula I are prepared by reducing a compound of the formula II in an inert solvent. The reduction can be carried out using a metal hydride, such as lithium aluminum hydride, lithium t-butoxy aluminum hydride, diborane and the like, preferably lithium aluminum hydride. Although the particular inert solvent used is not critical, it is preferred that the reaction be carried out in ethers, such as diethyl ether, dioxane and the like, especially tetrahydrofuran. The temperature at which the reaction is carried out is not critical, but it is preferred that the reaction be carried out between about 35° to 120° C., perferably at the reflux temperature of the reaction media. The time of the reaction also is not critical, but it is preferred that the reacion be run for 2 to 8 hours, especially about 4 hours. It is also preferred that the reaction be carried out in an inert atmosphere such as argon, helium, or nitrogen, preferably nitrogen. The compounds of formula (I) are isolated by conventional techniques, e.g., evaporation and recrystallization.

The compound of formula (II) and the corresponding compound in which R₃ is hydrogen may be prepared in accordance with the following reaction scheme:

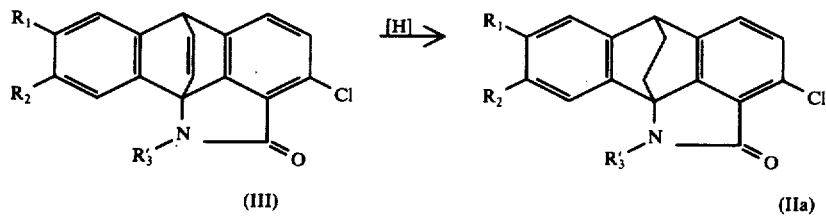

where
R₃' is hydrogen, methyl or ethyl and
R₁ and R₂ are as defined above.

The compounds of formula (IIa) are prepared by reducing a compound of the formula III with hydrogen in an inert solvent in the presence of a hydrogenation catalyst. The catalyst can be any of the standard hydrogenation catalysts, perferably palladium or platinum, neat or supported on carbon, e.g., 5 or 10 percent palladium on carbon or alumnina or platinum oxide. The specific solvent used is one that is inert to hydrogenation, such as acetic acid, alcohols of 1 to 4 carbon atoms, and the like. The temperature at which the reaction is carried out is not critical, but it is perferred that the reaction be carried out between about 20° to 40° C., perferably at about room temparature The reaction is run until the uptake of hydrogen is complete. It is preferred that the reaction be carried out under 1 to 5 atmosphere of hydrogen. The compounds of formula (IIa) are isolated by conventional techniques, e.g., evaporation and recrystallization.

The compound of formula (III) and (IIa) which R₃' is lower alkyl may be prepared in accordance with the following reaction scheme:

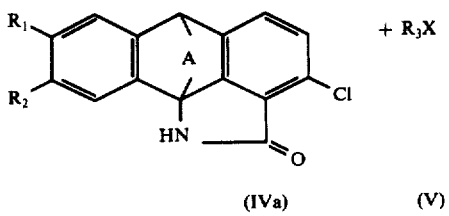 + R₃X 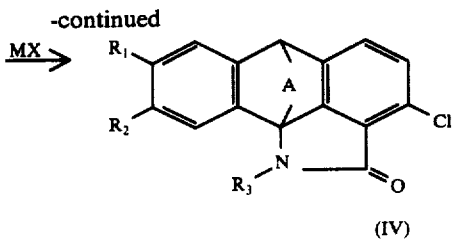

(IVa)　(V)　　　　　　　　　(IV)

where
A is —CH₂—CH₂— or —CH=CH—,
X is chlorine, bromine, or iodine and
R₁, R₂, and R₃ are defined above.

The compounds of formula (IV) are prepared by reacting a compound of formula (IVa) with a compound of the formula (V) in an inert solvent in the presence of an alkali metal hydride.

The alkali metal hydride can be lithium, sodium, or potassium hydride, preferably sodium hydride, and it is preferred that the compound of formula (IVa) be heated with the alkali metal hydride at about 50° to 90° C, preferably 60° to 80° C., for about 1 to 4 hours prior to the addition of the compound of formula (V). Although the particular solvent used is not critical, it is preferred that the reaction be carried out in an aliphatic or aromatic solvent, such as hexane, heptane, benzene, xylene, toluene, and the like, dimethylformamide, dimethylacetamide, dimethyl sulfoxide, tetrahydrofuran, or mixtures thereof. The temperature at which the reaction is carried out is not critical, but it is preferred that the reaction be carried out between about 5° to 35° C., preferably between about 10° to 20° C. The time of the reaction also is not critical, but it is perferred that the reaction be run for 6 to 18 hours. It is also preferred that the reaction be carried out in an inert atmosphere such as argon, helium, or nitrogen, preferably nitrogen. The compounds of formula (IV) are isolated by conventional techniques, e.g., chromatography and crystallization.

The compound of formula (IVa) in which A is —CH=CH—may be prepared in accordance with the following reaction scheme:

ferred that the reaction be carried out between about −55° to −45° C., especially about −50° C. The time of the reaction is not critical, but it is preferred that the reaction be run for about 0.2 to about 1.0 hours It is also preferred that the reaction be carried out in an inert atmosphere such as argon, helium, or nitrogen, preferably nitrogen. The compound of formula (IVb) is isolated by conventional techniques, e.g., filtration and crystallization.

The compound of formula (V), (VII) and many of the compounds of formula (VI) are known and may be prepared by methods described in the literature. The compounds of formula (VI) not specifically disclosed may be prepared by analogous methods using known starting materials.

The compounds of formula (I) and (IIa) are useful because they possess pharmacological activity in animals. In particular, the compounds of formula (I) are useful as anti-inflammatory agents, as indicated by their activity in rats dosed orally with 6.3 to 100 milligrams per kilogram of animal body weight of the test compound 1 hour before administration ofcarrageenan. The resulting edema is measured 3 hours after carrageenan administration by substantially the procedure described by Winter (Proc. Soc. Exptl. Biol., 111:544, 1962).

When the compounds are employed for the above utility, they may be combined with one or more pharmaceutically acceptable carriers or adjuvants, and may be administered orally in such forms as tablets, capsules, dispersible powders, granules, syrups, elixirs, suspensions, and the like, or parenterally in the form of an injectable solution or suspension. These pharmaceutical preparations may contain from about 0.5 percent to

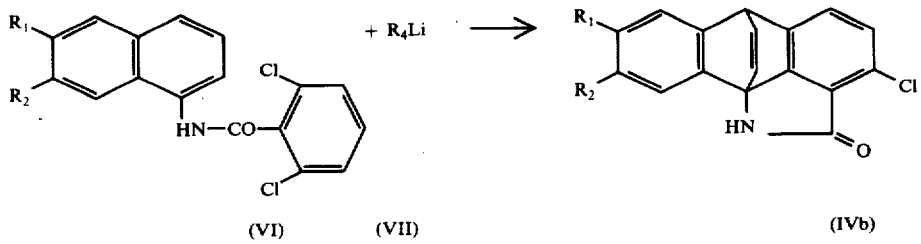

(VI)　(VII)　　　　　　　　　(IVb)

where
R₄ is alkyl of 1 to 6 carbon atoms or phenyl and
R₁ and R₂ are as defined above.

The compounds of formula (IVb) are prepared by reacting a compound of the formula (VI) with a compound of the formula (VII) in an inert solvent at a temperature of between about −75° to about −40° C. Although the particular inert solvent used is not critical, it is preferred that the reaction be carried out in ethers such as diethyl ethers, tetrahydrofuran, dioxane, and the like or hydrocarbons, such as hexane, heptane, benzene, and the like. The particular temperature at which the reaction is carried out is also not critical, but it is preabout 90 percent by weight based on the final composition of the active ingredient in combination with the carrier or adjuvant.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid; and accordingly, are included within the scope of the invention. Representative of the acid addition salts are the mineral acid salts, such as the hydrochloride, hydrobromide, sulfate, phosphate, and the like and the organic acid salts, such as the succinate, benzoate, acetate, p-toluenesulfonate, benzenesulfonate, and the like.

The anti-inflammatory effective dosage of the compounds of formula (I) and (IIa) will depend on the particular compound employed, the method of administration and the severity of the condition being treated. In general, satisfactory results are obtained when these compounds are administered in the treatment of inflammations at a daily dosage of about 7 milligrams to about 700 milligrams per kilogram of animal body weight, preferably orally. This daily dosage is preferably administered 2 to 4 times a day, or in sustained release form. For most large mammals, such as primates, the total daily dosage is from about 500 milligrams to about 4.0 milligrams. Dosage forms suitable for internal use comprise from about 125 milligrams to about 2.0 milligrams of the active compound in intimate admixture with a solid or liquid pharmaceutically acceptable carrier or diluent.

A representative formulation suitable for oral administration 2 to 4 times a day in the treatment of inflammation is a capsule prepared by standard encapsulating techniques which contains the following:

| INGREDIENTS | WEIGHT (mg.) |
|---|---|
| 3-chloro-1-methyl-1,2-dihydro-6,10b-ethanodibenzo[cd,g]indole hydrochloride | 500 |
| Inert solid diluent (starch, lactose, kaolin) | 500 |

EXAMPLE 1

3-chloro-1-methyl-1,2-dihydro-6,10b-ethanodibenz[cd,g]indole

Step A:
3-chloro-6,10b-ethanodibenzo[cd,g]indol-2(1H)-one

A solution of 18.95 grams (0.06 mole) of N-(1-naphthyl-2,6-dichlorbenzamide in 120 milliliters of dry tetrahydrofuran is blanketed under nitrogen and cooled to −50° C. in a dry ice-acetone bath. The mixture is then stirred and treated dropwise with 57.4 milliliters (0.12 mole) of n-butyllithium in hexane at −50° ±5° and held at −45° for 0.5 hours. The cooling bath is then removed and when the temperature reaches −20°, the mixture is treated with 2N-hydrochloric acid until the solution is acidic. The mixture is filtered and the resultant solid is crystallized from acetone-benzene to give 3-chloro-6,10b-ethenodibenzo[cd,g]indole-2(1H)-one, (m.p. > 280° C.).

When the above procedure is carried out using an equivalent amount of N-(6-methyl-1-naphthyl)-2,6-dichlorobenzamide, N-(7-methyl-1-naphthyl)-2,6-dichlorobenzamide or N-(6,7-dimethyl-1naphthyl)-2,6-dichlorobenzamide in place of the N-(naphthyl-2,6-dichlorobenzamide, there is obtained 3-chloro-8-methyl-6,10b-ethenodibenzo[cd,g]indol-2(1H)-one; 3-chloro-9-methyl-6,10b-ethenodibenzo[cd,g]indole-2(1H)-one or 3-chloro-8,9-dimethyl-6,10b-ethenodibenzo[cd,g]indol-2(1H)-one, respectively.

Step B:
3-chloro-6,10b-ethanodibenzo[cd,g]indol-2-(1H)-one

Into a pressure bottle is charged 0.1 gram of platinum oxide, 250 milliliters of acetic acid and 5.40 grams (0.019 mole) of 3-chloro-6,10b-ethenodibenzo[cd,g]indol-2(1H) one. The solution is then hydrogenated in a Parr Hydrogenation apparatus at 50 p.s.i. of hydrogen and room temperature. After the hydrogen uptake is completed, the mixture is filtered through celite and the filtrate concentrated in vacuo. The residue is crystallized from acetone-benzene to give 3-chloro-6,10b-ethanodibenzo[cd,g]indol-2-(1H)-one (m.p. 234° C.)

Following the above procedure, but using an equivalent amount of: 3-chloro-8-methyl-6,10b-ethenodibenzo[cd,g]indol-2 (1H)-one; 3-chloro-9-methyl-6,10b-ethenodibenzo[cd,g]indol-2 (1H)-one; or 3-chloro-8,9-dimethyl-6,10b-ethenodibenzo[cd,g]indol-2 (1H)-one in place of the above 3-chloro-6,10b-ethenodibenzo[cd,g]indol-](1H)-one, there is obtained: 3-chloro-8-methyl-6,10b-ethanodibenzo[cd,g]indol-2 (1H)-one; 3-chloro-9-methyl-6,10b-ethanodibenzo[cd,g]indol-2 (1H)-one; or 3-chloro-8,9-dimethyl-6,10b-ethanodibenzo[cd,g]indol-2 (1H)-one, respectively.

Step C:
3-chloro-1-methyl-6,10b-ethanodibenzo[cd,g]indole-2 (1H)-one

Into a flask equipped with a stirrer and condenser and maintained under a nitrogen blanket are charged 1.5 grams (0.07 mole) of sodium hydride, 60 milliliters of anhydrous dimethylformamide and 6 milliliters of anhydrous toluene. The mixture is stirred and heated at 90° for one hour and then cooled to 10°. A solution of 14.1 grams (0.05 mole) of 3-chloro-6,10b-ethanodibenzo[cd,g]indol-2(1H)-one in 25 milliliters of dry dimethylformamide is then added dropwise. The reactants are maintained at 65°±5° for 3 hours, then cooled in an ice bath to 10° and treated with 5 milliliters of methyl iodide in 25 milliliters of dry dimethylformamide. After standing overnight at room temperature, the mixture is filtered and the filtrate concentrated in vacuo. The residue is dissolved in toluene-acetone, and chromatographed in a silicon gel column. Elution with toluene acetone gives 3-chloro-1-methyl-6,10b-ethanodibenz[cd,g]indole-2 (1H)-one (m.p. 161° C.).

When the above process is carried out using in place of the 3-chloro-6,10b-ethanodibenzo[cd,g]indol-2 (1H)-one an equivalent amount of: 3-chloro-8-methyl-6,10b-ethanodibenzo [cd,g]indol-2 -(1H)-one; 3-chloro-9-methyl-6,10b-ethanodibenzo [cd,g]indol-2 (1H)-one; or 3-chloro-8,9-dimethyl-6,10b-ethanodibenzo [cd,g]indol-2 (1H)-one; there is obtained: 3-chloro-1,8-dimethyl-6,10b-ethanodibenzo[cd,g]indol-2 (1H)-one; 3-chloro-1,9-dimethyl-6,10b-ethanodibenzo[cd,g]indol-2 (1H)-one; or 3-chloro-1,8,9-trimethyl-6,10b-ethanodibenzo[cd,g]indol-2 (1H)-one, respectively.

Step D:
3-chloro-1-methyl-1,2-dihydro-6,10b-ethanodibenzo[cd,g]indole

Into a flask equipped with a stirrer, dropping funnel, condenser, and maintained under a nitrogen blanket is charged 1.0 grams (0.02 mole) of lithium aluminum hydride and 50 milliliters of dry tetrahydrofuran. This mixture is stirred and a solution of 4.64 grams (0.016 mole) of 3-chloro-1-methyl-6,10b-ethanodibenzo [cd,g]indol-2 (1H)-one in 60 milliliters of tetrahydrofuran is added dropwise over a period of about 0.5 hours. The mixture is then gently refluxed for 4 hours, after which it is cooled with an ice bath to 5° and treated dropwise with 2 milliliters of 2N sodium hydroxide and 3 milliliters of water and about 15 grams anhydrous sodium sulfate. The mixture is filtered through celite and the cilite-cake is washed with dry tetrahydrofuran. The combined tetrahydrofuran filtrates are concentrated in vacuo, and the residue is dissolved in diethyl ether and treated with a stream of anhydrous hydrogen chloride gas. The solid precipitate is filtered off and dried to give 3-chloro-1-methyl-1,2-dihydro-6,10b-ethanodibenzo[cd,g]indol hydrochloride (m.p. > 250° C.).

Following the above procedure, bit using in place of the 3-chloro-1-methyl-6,10b-ethanodibenzo[cd,g]indol-2 (1H)-one, an equivalent amount of: 3-chloro-1,8-dimethyl-6,10b-ethanodibenzo [cd,g]indol-2 (1H)-one; 3-chloro-1,9-diemthyl-6,10b-ethanodibenzo [cd,g]indol-2 (1H)-one; or 3-chloro-1,8,9-trimethyl-6,10b-ethanodibenzo [cd,g]indol2 (1H)-one, there is obtained the hydrochlodride salt of 3-chloro-1,8-dimethyl-1,2-dihydro-6,10b-ethanodibenzo [cd,g]indole; 3-chloro-1,9-dimethyl-1,2-dihydro-6,10b-ethanodibenzo [cd,g]indole; or 3-chloro-1,8,9-trimethyl-1,2-dihydro-6,10b-ethanodibenzo [cd,g]indole, respectively.

EXAMPLE 2

3-chloro-1-methyl-1,2-dihydro-6,10b-ethanodibenzo[cd,g]indole

Into a flask equipped with a stirrer is charged 4.8 grams (0.2 mole) of sodium hydride, 500 milliliters of dry dimethylformamide, 100 milliliters of dry xylene and a solution of 28.0 grams (0.10 mole) of 3-chloro-6,10b-ethenodibenzo[cd,g]indol-2-(1H)-one, prepared as in Step A of Example 1 in 200 milliliters of dry dimethylformamide. The mixture is blanketed with nitrogen, heated to 80° for 1.5 hours and then cooled in an ice bath to 10°. A solution of 57 grams (0.4 mole) of methyl iodide in 25 milliliters of dimethylformamide is then added dropwise at 10° to 15°. The mixture is allowed to stand overnight (about 15 hours) at room temperature following which it is filtered and evaporated in vacuo. The residue is dissolved in hot toluene, treated with charcoal and then filtered through cilite. The toluene of the filtrate is removed in vacuo and the residue crystallized from isopropanol to give 3-chloro-1-methyl-6,10b-ethyenodibenzo[cd,g]indol-2(1H)-one, (m.p. 158°-159° C).

Following the procedures of Steps B and D of Example 1 with the above 3-chloro-1-methyl-6,10b-ethenodibenzo [cd,g]indol-2(1H)-one, there is obtained 3-chloro-1-methyl-1,2-dihydro-6.10 b-ethanodibenzo[cd,g]indol as the final product.

What is claimed is:

1. A compound of the formula:

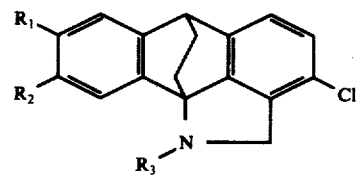

where
R₁ and R₂ each independently are hydrogen or straight chain lower alkyl of 1 to 3 carbon atoms and
R₃ is methyl or ethyl or
a pharmaceutically acceptable acid addition salt thereof.

2. The compound of claim 1, which is 3-chloro-1-methyl-1,2-dihydro-6,10b-ethanodibenzo[cd,g]indole.

3. A pharmaceutical composition useful in treating inflammation comprising 0.5 to 4.0 grams of a compound of claim 1 or a pharmaceuticaly acceptable acid addition salt thereof in association with a pharmaceutical carrier.

4. A method of treating inflammation in animals which comprises administering to an animal in need of said treatment a therapeutically effective amount of a compound of claim 1 or a pharmaceutically acceptable acid addition salt thereof.